United States Patent
Bowman et al.

(10) Patent No.: US 6,489,500 B2
(45) Date of Patent: Dec. 3, 2002

(54) CONTINUOUS TRANSESTERIFICATION PROCESS FOR ALKOXYORGANOSILICON COMPOUNDS

(75) Inventors: Mark P. Bowman, New Kensington, PA (US); Thomas E. Childress, Newport, OH (US); Frank D. Mendicino, Marietta, OH (US); R. Ingrid Warren, Vincent, OH (US)

(73) Assignee: Crompton Corporation, Greenwich, CT (US)

( * ) Notice: Subject to any disclaimer, the term of this patent is extended or adjusted under 35 U.S.C. 154(b) by 0 days.

(21) Appl. No.: 10/081,192

(22) Filed: Feb. 25, 2002

(65) Prior Publication Data

US 2002/0123640 A1 Sep. 5, 2002

Related U.S. Application Data

(60) Provisional application No. 60/272,909, filed on Mar. 2, 2001.

(51) Int. Cl.$^7$ .................................................. C07F 7/08
(52) U.S. Cl. ...................................................... 556/469
(58) Field of Search .......................................... 556/469

(56) References Cited

U.S. PATENT DOCUMENTS

| | | | | |
|---|---|---|---|---|
| 4,298,753 | A | 11/1981 | Schinabeck et al. | 556/415 |
| 4,709,067 | A | 11/1987 | Chu et al. | 556/440 |
| 4,762,939 | A | 8/1988 | Mendicino | 556/470 |
| 4,924,022 | A | 5/1990 | Bank et al. | 556/471 |
| 4,948,888 | A | * 8/1990 | Greco et al. | 556/469 |
| 5,041,595 | A | 8/1991 | Yang et al. | 556/479 |
| 5,559,264 | A | 9/1996 | Bowman et al. | 556/479 |
| 6,005,132 | A | 12/1999 | Weidner et al. | 556/469 |
| 6,015,920 | A | 1/2000 | Schilling et al. | 556/479 |

* cited by examiner

*Primary Examiner*—Paul F. Shaver

(57) ABSTRACT

A process is disclosed for the continuous transesterification of alkoxysilanes wherein an alkoxysilane is transformed to a different alkoxysilane in the presence of a catalyst and at least one alcohol that provides the different alkoxy group.

17 Claims, No Drawings

CONTINUOUS TRANSESTERIFICATION PROCESS FOR ALKOXYORGANOSILICON COMPOUNDS

CROSS REFERENCE TO RELATED APPLICATIONS

We claim the benefit under Title 35, United States Code, § 120 of U.S. Provisional Application Ser. No. 60/272,909, filed Mar. 2, 2001, entitled CONTINUOUS TRANSESTERIFICATION PROCESS FOR ALKOXYORGANOSILICON COMPOUNDS.

BACKGROUND OF THE INVENTION

1. Field of the Invention

The present invention relates to a continuous transesterification process. More particularly, the present invention relates to a continuous transesterification process for the conversion of alkoxysilanes to different alkoxysilanes.

2. Description of Related Art

The major portion of the chemical industry involved in the production of organofunctional silicon compounds has been working on processes and products that do not involve the handling of hazardous chlorositanes as raw materials. The direct preparation of hydroalkoxysilanes from alcohols and silicon metal (see for example, U.S. Pat. No. 4,762,939) as shown in Reaction (I) avoids the preparation of chlorosilanes as was done in the older, two-step, process shown in Reactions (IIa) and (IIb), involving the preparation of trichlorosilane from hydrogen chloride and silicon metal followed by its esterification to the corresponding hydroalkoxysilane.

(I)

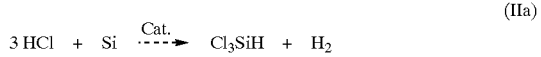

(IIa)

(IIb)

Hydroalkoxysilanes are useful in a variety of hydrosilation reactions, of the kind shown in Reaction (III), known to and practiced by those skilled in the art to provide commercially useful organofunctional silicon compounds:

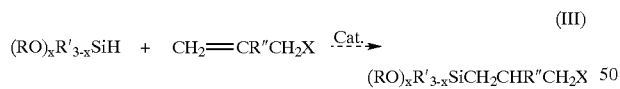

(III)

where, for example, R is a hydrocarbon group or a substituted hydrocarbon group, R' is R, R" is H or R, and X is a functional group, including Cl, $NH_2$, NHR, $O_2CCMe=CH_2$, an epoxy-group containing moiety, and the like, and x is 1, 2, or 3.

Recent advances in the technology of hydrosilation reactions of hydroalkoxysilanes have provided such organofunctional silicon compounds in economically attractive yields (see, for example, U.S. Pat. Nos. 4,709,067, 5,041,595, and 5,559,264), overcoming earlier, well-recognized deficiencies, particularly for the hydrosilation of allyl chloride (U.S. Pat. No. 5,559,264).

Nevertheless, a problem remains in that the production efficiencies are highest when R is a methyl group, such that the ROH above is methanol, and the $(RO)_3SiH$ is trimethoxysilane, but various applications of organofunctional silicon compounds require other R groups derived from other alcohols for reasons of reactivity, stability, toxicity, volatility, solubility, and flammability, among others. Other R groups that are useful in products include ethyl, propyl, isopropyl, butyl, 2-methoxyethyl, and the like. Thus, there is a need in the industry for a highly efficient process for transforming lower alkoxy groups attached to silicon, such as methoxy groups, to higher alkoxy groups, such as ethoxy groups, to provide a variety of organofunctional silicon compounds as may be required for a particular use. There is also, on occasion, a separate need for the reverse process, i.e., the transformation of higher alkoxy groups to lower alkoxy groups. For reasons of high reaction rates, high efficiencies, and lower capital investments, such a process, heretofore known in the art only in batch or non-continuous modes, should be of a continuous nature. While continuous processes exist for the conversion of chlorosilanes to alkoxysilanes, e.g., esterification (Reaction (IIb) see, for example, U.S. Pat. Nos. 4,298,753 and 4,924,022), continuous technology does not appear to have been applied to transesterification, i.e., the replacement of one alkoxy group with another, even by organizations knowledgeable in continuous esterification technology (see U.S. Pat. No. 6,005,132 wherein the continuous removal of lower alcohol is disclosed, but the process itself is not continuous, i.e., all the higher alcohol is fed at once at the start). Batch transesterification is well known in the art, but is prone to long reaction times or lower efficiencies relating to the use of excess alcohol to provide the desired alkoxy group in a reasonable reaction time.

There is also a need to perform such continuous transesterification processes in giving consideration to minimized economics, including the minimized generation of hazardous wastes. This can be accomplished by the use of recycled raw materials and/or materials of lower purity, or through the performance of more than one process step concurrently, as by combining the neutralization of a feed stream with transesterification of the bulk of that stream, or by transesterification of more than one alkoxysilane concurrently, with later separation of the products, as by simple distillation.

SUMMARY OF THE INVENTION

The present invention provides a process for the conversion of alkoxysilanes to different alkoxysilanes, i.e., transesterification, that is efficient and continuous and can be practiced in commercially available equipment designed for continuous operation. The process comprises the reaction of an alkoxyorganosilicon compound containing at least one alkoxy group with one or more alcohols that provide different alkoxy groups on silicon according to Equation (IV).

(IV)

wherein R and R' are independently selected from the group consisting of unsubstituted and substituted hydrocarbon moieties and are different from one another. The other three bonds on the silicon in Reaction (IV) can be to the same or other alkoxy groups, hydrocarbon groups, functionalized hydrocarbon groups (as in the products of Reaction (III), silicon-containing moieties, and even halogen groups (esterification of Si-halogen groups may occur concurrently with transesterification of alkoxy groups on silicon).

More particularly, the present invention is directed to a method for the continuous transesterification of alkoxysilanes comprising reacting at least one alkoxyorganosilicon compound containing at least one alkoxy group with at least one alcohol that provides at least one different alkoxy group on the silicon in the presence of an effective amount of an acidic or basic transesterification catalyst at an elevated temperature with continuous separation of product streams.

The process of the present invention is not narrowly limited and is thus applicable to a very large variety of alkoxyorganosilicon compounds, including monomeric silanes having one to four alkoxy groups, silanes containing more than one silicon atom, including oligomers and polymers, alkoxysiloxanes, and alkoxypolysiloxanes, as well as blends or mixtures thereof

DESCRIPTION OF THE PREFERRED EMBODIMENTS

The process of the present invention is a continuous process for the interconversion of alkoxysilanes, i.e., transesterification, according to the general Equation IV above. More specifically, when the alkoxysilane is a monomeric silane, said transesterification is expressed by Equation V, wherein R and R' are as defined above and $R^2$ is the same as or different from R or R'.

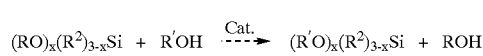
$$(RO)_x(R^2)_{3-x}Si + R'OH \xrightarrow{Cat.} (R'O)_x(R^2)_{3-x}Si + ROH \quad (V)$$

with the added proviso that R and R' contain no functional group that will not remain largely intact during the transesterification, and x is as defined above.

The process of the present invention can be performed in a variety of commercially available continuous units, including those typically used for continuous esterification, such as those described in U.S. Pat. No. 4,924,022, or in custom-designed commercial or laboratory scale units. Continuous stirred tank reactors, alone or in series, can be used, as can units designed for continuous countercurrent reactive distillation. Said units can be operated at or near atmospheric pressure, under vacuum, or under positive pressure; the choice being determined by the boiling points of the reactants and the desired operating temperature. The operating temperature will typically be an elevated temperature to maximize reaction rates and boiling point differences between reactants and products. Preferably, the elevated temperature is at least the boiling point of the lowest boiling alcohol at reaction pressure.

The catalysts operable in the present invention include those typically used for batch esterifications and transesterifications, i.e., acids and bases. The catalyst selection is determined in part by the alkoxysilane being transesterified. For example, an aminoalkylalkoxysilane would normally be transesterified with a basic catalyst, such as the corresponding sodium alkoxide, while a silane containing non-functional or base-sensitive alkyl or alkoxy groups would be transesterified with an acid catalyst, such as toluenesulfonic acid. When the concurrent neutralization or removal of halosilane groups is practiced, either an acid catalyst is used or sufficient base catalyst is employed to account for losses to reactions with halosilanes. The catalysts can be heterogeneous, in the form of pellets or beads, depending on equipment design, or homogeneous, i.e., completely soluble in the reaction medium. The concentration of the transesterification catalyst is not narrowly critical, and can be in the range of from about 0.001 to about 1.0% by weight relative to the alkoxyorganosilicon compound. Preferably, the transesterification catalyst is soluble in the reaction medium at a level of 0.001 to 1.0 % by weight of the alkoxyorganosilicon compound.

The alcohols used in the present invention include a wide range of hydroxyl-functional hydrocarbons, including methanol, ethanol, propanol, isopropanol, isomers of butanol, allyl alcohol, 2-methoxyethanol, benzyl alcohol, diols, and the like with the provisos that the alcohol must be stable under transesterification conditions and must not be so sterically hindered as to prevent reaction. When the lower and higher alcohols have boiling points that are relatively close, such as methanol and ethanol, the ethanol fed to the reactor can, if desired, contain some methanol, e.g., it may be a recycle stream or impure stream from some other process that is fed to the continuous reactor at a point where the reaction in progress contains both methanol and ethanol. Thus, the total feed of higher alcohol need not be high in purity to make pure products. The relative purities of the lower and higher alcohols may, as a practical matter, be determined by the purity needs of the products, and whether or not they are to be further purified, as by distillation. Typically, an excess of the transesterifying alcohol is used, and the excess can be up to 100% or more on a molar basis relative to the alkoxy groups being transesterified. This necessitates at least a partial purification of the continuously separated alcohol stream for purposes of recycling.

The alkoxysilane raw materials, as well as the alkoxysilane products, can be monomeric silicon compounds, dimers, trimers, oligomers, or polymers, and when not monomers, can contain the same or different siloxane units. Thus, any alkoxyorganosilicon compound known in the art can be considered to be within the contemplated application of the method of the instant invention, with the provisos that the compound should not contain functional groups that will not largely survive the transesterification reaction conditions, and the alkoxy group being transesterified must not be so sterically hindered so as to avoid reaction. Specifically included are the organofunctional trialkoxysilanes, the organofunctional alkyldialkoxysilanes, and the organofunctional dialkylalkoxysilanes.

The alkoxysilane raw materials can also be blends or mixtures and can contain impurities. For example, the alkoxysilane raw material can be the product stream from a different process, such as the product stream from the hydrosilation of allyl chloride with trimethoxysilane. This stream (see U.S. Pat. Nos. 5,559,264 and 6,015,920) is known to contain low levels of chlorosilyl groups and tetramethoxysilane in addition to product, 3-chloropropyltrimethoxysilane. When this stream is transesterified with ethanol, chlorosilyl groups are concurrently converted to ethoxysilyl groups and the resultant product becomes largely a mixture of tetraethoxysilane and 3-chloropropyltriethoxysilane, which can be purified as needed, as by distillation.

In a similar vein, tetramethoxysilane may be introduced, as a by-product from the direct reaction of methanol with silicon metal, with 3-chloropropyltrimethoxysilane to yield the same mixture of products. Alternatively, chlorosilyl groups may be present as an added raw material, such that reaction of a mixture of 3-chloropropyltrimethoxysilane and 3-chloropropyltrichlorosilane with ethanol to yield 3-chloropropyltriethoxysilane is within the scope of the instant invention.

In one aspect of the present invention, the alkoxyorganosilicon compound comprises a minor proportion of a halosilane group or a minor proportion of a halosilane compound.

In a preferred aspect of the present invention, the alkoxyorganosilicon compound is selected from the group consisting of sulfur-containing silanes and amino-group containing silanes.

It is recognized that for most functional silane products, the content of transesterified alkoxy groups may not be 100% of theory, and that there may be some low percentage of non-transesterified alkoxy groups. The allowable level will be determined by the performance requirements of a particular product.

While the process of the present invention does not inherently require a solvent, a solvent can present, and can assist the process as by forming lower boiling azeotropes with one or more of the reactants or products.

Those skilled in the art will recognize the very wide ranges of equipment, reactants, catalysts, and reaction conditions under which the process of the present invention can be practiced. It is also recognized that the transesterification reactions performed by the practice of the present invention need not be quantitative, and that products may contain minor amounts of the starting alkoxy groups. Owing to the continuous nature of the process of the present invention, product of lower purity can be reintroduced to the reactor to drive the transesterification more toward the desired product. Similarly, the mixed alcohol streams taken overhead can be separated by well-known methods to the extent desired and reused, further increasing process efficiency.

Various features and aspects of the present invention are illustrated further in the examples that follow. While these examples are presented to show one skilled in the art how to operate within the scope of the invention, they are not intended in any way to serve as a limitation upon the scope of the invention.

EXAMPLES

Example 1

Transesterifications of Functional Alkoxysilanes

An apparatus consisting of an appropriately fitted glass flask attached to the bottom of a 15 tray Oldershaw column, with a distillation head and addition funnel fitted to the top of the column, was assembled. The flask was charged with 202.2 grams of vinyltriethoxysilane, which was heated to 150° C. under a nitrogen atmosphere. Over a period of 6 hours, vinyltrimethoxysilane (906.6 grams, containing 1.81 grams of para-toluenesulfonic acid monohydrate (2000 parts per million based on vinyltrimethoxysilane) was fed at the top of the column concurrently with ethanol (1555 grams) being fed to the flask at the bottom of the column. Product was removed via a bottom take-off valve from the flask at hourly intervals, with 220.3 grams remaining in the flask at the end of the reaction, nearly corresponding to the initial charge of vinyltriethoxysilane. The product samples totaled 763 grams of vinyltriethoxysilane of 90% purity. The alcohol stream being continuously removed from the top of the column consisted of methanol, ethanol, and 15% to 50% of mixed vinyltrialkoxysilanes, depending on the head temperature (71° C. to 100° C.) at which the alcohol stream was removed. The vinyltrialkoxysilanes in the overhead stream are recoverable in subsequent runs, as are the methanol and ethanol, after separation.

Under similar conditions in the same apparatus, 3-mercaptopropyltrimethoxysilane containing para-toluenesulfonic acid monohydrate was converted to 3-mercaptopropyltriethoxysilane at greater than 90% purity, and 3-aminopropyltriethoxysilane containing sodium methoxide as catalyst was converted to 3-aminopropyltrimethoxysilane of greater than 90% purity. The latter reaction exemplifies replacement of a higher alkoxy group with a lower alkoxy group.

Example 2

Larger Scale Transesterification

An apparatus consisting of a dual column countercurrent reactive distillation system was assembled from two appropriately fitted glass flasks fitted to the bottoms of two 2" by 96" packed columns. While ethanol was fed continuously to the bottom of both columns, 3-chloropropyltrimethoxysilane was fed continuously to the top of the first column, and the contents of the first flask fed continuously to the top of the second column, with product being removed from the second flask. When steady state operation was achieved, 3-chloropropyltriethoxysilane of greater than 95% purity was produced at a rate of 3 lb/hr. p-Toluenesulfonic acid monohydrate was used as the transesterification catalyst.

Similar product, containing less than 0.3% 3-chloropropylmethoxydiethoxysilane, was prepared under similar conditions except that an ethanol/methanol mixture (96% ethanol) was fed at midpoint of the first column with pure ethanol being fed to its bottom flask and dodecylbenzenesulfonic acid (0.2 wt-% relative to starting silane) was used as the transesterification catalyst. This demonstrates the effective use of a less pure recycle stream, which is significant, since 100% molar excess of ethanol is used. 3-Chloropropyltriethoxysilane of similar relative purity (low 3-chloropropylmethoxydiethoxysilane content) was prepared when the feed contained several percent tetramethoxysilane, providing 7% tetraethoxysilane in the product stream.

In view of the many changes and modifications that can be made without departing from principles underlying the invention, reference should be made to the appended claims for an understanding of the scope of the protection to be afforded the invention.

What is claimed is:

1. A method for the continuous transesterification of alkoxysilanes comprising reacting at least one alkoxyorganosilicon compound containing at least one alkoxy group with at least one alcohol that provides at least one different alkoxy group on the silicon in the presence of an effective amount of an acidic or basic transesterification catalyst at an elevated temperature with continuous separation of product streams.

2. The method of claim 1 wherein the alkoxyorganosilicon compound is a mixture of more than one alkoxysilane.

3. The method of claim 1 wherein the transesterification catalyst is soluble in the reaction medium at a level of 0.001 to 1.0 % by weight of the alkoxyorganosilicon compound.

4. The method of claim 1 wherein the elevated temperature is at least the boiling point of the lowest boiling alcohol at reaction pressure.

5. The method of claim 1 wherein the at least one alcohol comprises alcohol that provides at least one different alkoxy group and the alcohol formed from the alkoxy group of the alkoxyorganosilicon compound.

6. The method of claim 1 wherein the alcohol comprises at least one alcohol from
   A) a recycle stream or
   B) from an impure stream from a different process.

7. The method of claim 1 wherein a higher alkoxy group is transesterified with a lower alkoxy group.

8. The method of claim 1 wherein the alkoxyorganosilicon compound comprises a minor proportion of a halosilane group or a minor proportion of a halosilane compound.

9. The method of claim 8 wherein the halogen of the halosilane group or the halosilane compound is chlorine.

10. The method of claim 1 wherein the alkoxyorganosilicon compound is vinyltrimethoxysilane and the product is vinyltriethoxysilane.

11. The method of claim 1 wherein the alkoxyorganosilicon compound is 3-chloropropyltrimethoxysilane and the product is 3-chloropropyltriethoxysilane.

12. The method of claim 11 wherein
   A) the 3-chloropropyltrimethoxysilane contains low levels of chlorosilane groups and tetramethoxysilane;
   B) the 3-chloropropyltriethoxysilane product contains tetraethoxysilane; and
   C) the catalyst is selected from the group consisting of p-toluenesulfonic monohydrate and dodecylbenzenesulfonic acid.

13. The method of claim 1 wherein the alkoxyorganosilicon compound is selected from the group consisting of sulfur-containing silanes and amino-group containing silanes.

14. The method of claim 13 wherein the alkoxyorganosilicon compound is a sulfur-containing silane.

15. The method of claim 14 wherein the alkoxyorganosilicon compound is 3-mercaptopropyltrimethoxysilane and the product obtained by the transesterification is 3 3-mercaptopropyltriethoxysilane.

16. The method of claim 13 wherein the alkoxyorganosilicon compound is an amino-group containing silane.

17. The method of claim 16 wherein the alkoxyorganosilicon compound is 3-aminopropyltriethoxysilane and the product obtained by the transesterification is 3-aminopropyltrimethoxysilane.

* * * * *